United States Patent [19]

LeRoy

[11] Patent Number: 4,788,427
[45] Date of Patent: Nov. 29, 1988

[54] FERTILIZATION DETECTION

[76] Inventor: Pierre L. LeRoy, 1101 N. Broom St., Wilmington, Del. 19806

[21] Appl. No.: 903,496

[22] Filed: Sep. 4, 1986

[51] Int. Cl.⁴ ............................................. G01N 21/00
[52] U.S. Cl. .................................... 250/330; 250/340; 374/124
[58] Field of Search ............... 250/330, 340, 334, 342; 356/53; 374/124

[56] References Cited

U.S. PATENT DOCUMENTS 2,310,682  2/1943  Dooley ................................ 250/341
2,451,577  10/1948  Roberts ................................ 356/58

FOREIGN PATENT DOCUMENTS 0144451  9/1982  Japan .................................. 374/124

OTHER PUBLICATIONS

"Barnes Infrared Camera", Bulletin 12-600 of the Barnes Engineering Company, Defense and Space Division (May 1963), pp. 1-12, (see especially p. 5).

Primary Examiner—Janice A. Howell
Assistant Examiner—Constantine Hannaher
Attorney, Agent, or Firm—Connolly & Hutz

[57] ABSTRACT

The present invention relates to improvements in test methods for determining if eggs, seeds or the like are fertile. This is accomplished through the use of thermography equipment which senses a temperature rise characteristic of a fertile egg or seed. The sensing can be visually observed or a thermograph can be made of the observation.

8 Claims, 1 Drawing Sheet

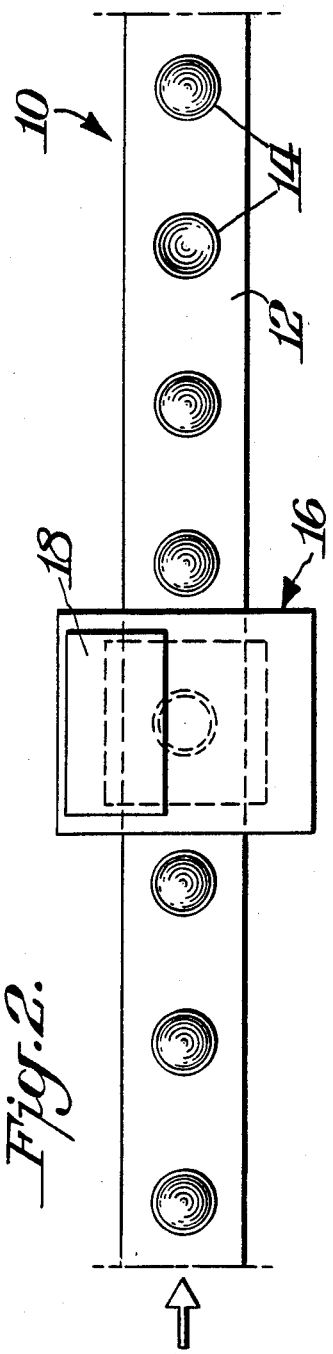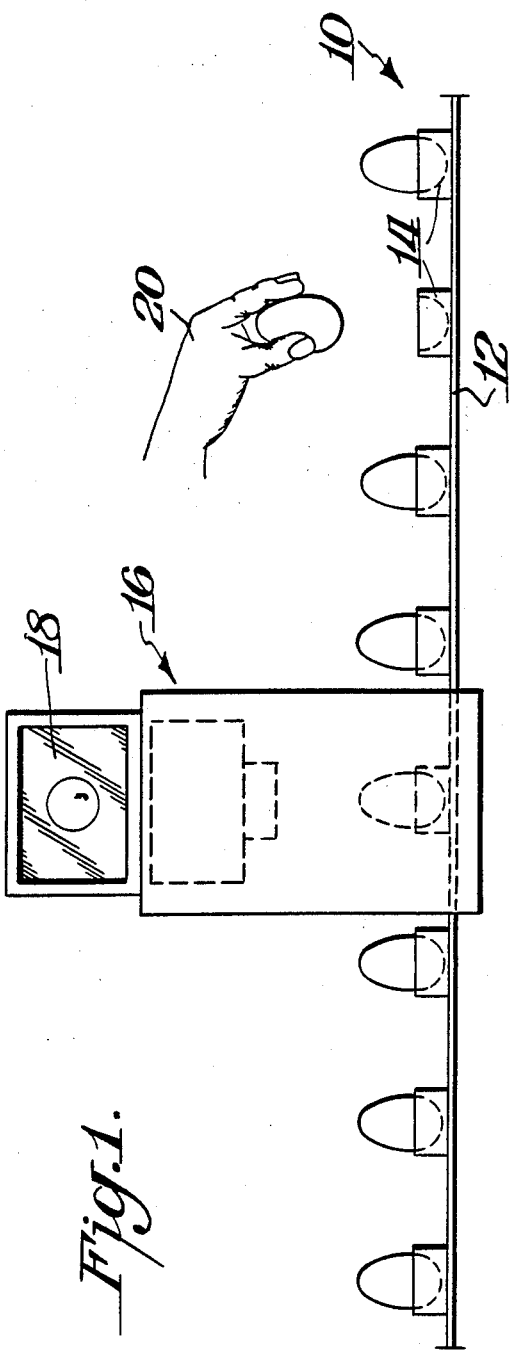

FERTILIZATION DETECTION

BACKGROUND OF THE INVENTION

The present invention relates to the fertilization detection of biological products such as eggs or seeds. In particular, the invention is directed to the detection of chicken eggs to determine if the eggs are fertile. It has been found that approximately from one-fourth to one-third of all eggs which are sent into a hatchery for incubation are not fertilized and are not detectible as unfertilized eggs until after 21 days of incubation has taken place. This consequently results in a tremendous waste of space, energy and labor in the poultry industry. It would be desirable if some convenient and reliable means could be utilized for quickly detecting whether or not an egg is fertile, whereupon unfertilized eggs could be removed from the incubation system so that the only eggs remaining are eggs which are definitely fertilized.

Similar concerns are had in other fields, such as in wildlife conservation programs, for example with duck, geese and swan eggs as well as other endangered species such as reptiles and turtle eggs. Additionally, it would be useful for other biological products such as banana crops or products involving seeds if it were know whether or not the seed is in fact fertilized.

SUMMARY OF INVENTION

An object of this invention is to provide a method and arrangement for detecting whether or not a biological product such as an egg or seed is fertilized.

A further object of this invention is to provide such a method and arrangement wherein the fertilization detection can be readily accomplished so that any unfertilized egg or seed which is detected can be quickly removed from the system and replaced by one which is fertilized.

In accordance with this invention thermography equipment is used for scanning the biological product where the product is fertilized. The heat detected by the thermographic equipment will result in a characteristic pattern which may be visually displayed or which may be displayed by a picture called a thermograph.

Where the invention is used in, for example, the poultry industry, individual eggs may be placed upright in a line in special containers on a conveyer belt. The conveyer belt carrying the eggs in turn passes below a thermograph scanner which may have a display window for indicating whether or not each passing egg is fertilized. The operator would then know the condition of each egg and with precision could immediately remove from the conveyer those eggs detected as being unfertilized. Accordingly, only eggs which have been detected as fertilized would remain in the incubation system.

THE DRAWINGS

FIG. 1 is a side elevation view of an arrangement in accordance with this invention; and FIG. 2 is a top plan view of the arrangement shown in FIG. 1.

DETAILED DESCRIPTION

The present invention is based upon the recognition that thermography provides a means of detecting whether or not various biological products such as eggs or seeds are fertilized. Thermography is an infrared, non-invasive heat detection process which has been used in industry, medicine, veterinary studies and agricultural applications. There, however, has been no application in the early detection of egg fertilization or seed fertilization using near, middle or far infrared testing ranges. The principle of thermography is based in the fact that any body above absolute zero temperature produces detectable heat emission patterns. Life processes such as those seen with disease states of chronic low back pain syndromes and other medical applications in neuropathic, vascular, skeletal and soft tissue disorders have been published.

Applicant has conducted studies to determine what resolution or how small a life object could be detected. It has been found possible to see down to the size of an algae cell. This is photosynthetic biological cellular unit that measures only 15 microns or is twice the size of a red blood cell. Applicant demonstrated different states of its active life processes based on photosynthesis. Applicant then turned his research to see if it were possible to detect early egg affect egg) fertilization employing thermographic techniques. The reasoning was that if 15 microns of metabolic activity could be demonstrated in algae, it should be possible to show early fertilization effect of an approximate 10 micron egg since fertilization would cause an increase in cellular metabolism; therefore should be detectable by thermographic scanning.

The following represents testing done in accordance with this invention.

Twenty ten-day old normal poultry eggs weighing 54 grams, incubated at 38° C. were thermographically scanned by a middle infrared 3.5 to 5.6 micron lens employing the AGA 780 System. The 20 eggs were compared to five similar but non-fertile control eggs.

The weight of the chick embryo at ten days is known to be three grams with an estimated cell mass measuring $1 \times 3$ cm and these were compared to the non-fertile eggs by the old standard candling method which have no thermally active bio-mass attributable to cell division.

The second part of the study compared healthy fertilized control eggs to an inoculated lethal virus variant number IBVD 1084 and thermographically compared to the control, otherwise intact healthy eggs with concentration of virus inoculation varying from $10^{-4}$ to $10^{-7}$ dilutions of the experimental virus.

The fertile eggs compared to non-fertile eggs showed an increase in thermal gradient profiles compared by blind technique. This study vividly demonstrates an active, characteristic hyperthermic "polar cap" over the "air cell", end of the egg, consistent with the known anatomic geographical area of egg embryogenesis at 240 hours of life with known cell mass of $1 \times 3$ cm.

Results of the second study demonstrates a characteristic lower thermal gradient pattern in the abnormal viral eggs showing in addition a constant lowering of the thermal gradient inversely proportional to the virus concentration. Finally terminating in end point reading when the embryo had ceased all cellular activity consistent with cell death. This infrared study permitted earlier detections of abnormal cell response before it could be ascertained clinically. This is consistent with the phenomena reported by Chavin and LeRoy in murine cancer virus inoculate.

The concepts of the invention described above are readily adaptable for use in the poultry industry. FIGS.

1-2 illustrate an arrangement 10. As illustrated arrangement 10 includes a conveyer belt 12 on which is detachable mounted a row of pockets or receptacles 14 which in conjunction with belt 10 form a continuous egg tray. As shown in FIGS. 1-2 arrangement 10 also includes a middle infrared thermography system 16 utilizing a scanning camera which is directed at the specially positioned egg trays for continuous scanning as the belt 12 moves through the scanning system 16. System 16 may be provided with a display screen 18 which would illustrate a pattern similar to a thermograph as each egg passes through the system. The operator would then immediately know whether each egg being inspected is fertilized or unfertilized. Accordingly, when an unfertilized egg is detected the operator 20 could simply remove that egg from its receptacle 14; the unfertilized egg could then be placed with other eggs for use such as with bakery companies or the like but would not be maintained in the incubation system and thus needlessly occupy space as well as take up energy and unnecessarily add to the cost of incubation.

Although FIGS. 1-2 illustrate an automatic system wherein there is an immediate visual inspection by an operator of the eggs passing through scanner 16 the concepts of this invention may be practiced for other purposes such as research for test purposes where the results of the inspection are exhibited on thermographs rather than a visual screen.

In the arrangements shown in FIGS. 1-2 a single row of eggs and egg receptacles is shown mounted on belt 12. Preferably, the eggs are arranged about three inches from pole to pole. A variation of the invention would be to include multiple rows of eggs which might for example be parallel to each other with the individual eggs however staggered. If desired, the individual eggs may also be in line with each other across belt 12. Such arrangement would include a plurality of screens for viewing by the operator 20. This arrangement would be more complicated and would require greater skill by the operator but it would lend itself to higher speed.

The invention may be practiced to provide improved thermal gradient testing for eggs that are diseased, injected with poultry viruses as well as thermographic examination of chick embryos for improved methods of treating diseased eggs which is also a serious poultry problem.

The invention is not limited to chicken eggs but may be used with other egg applications such as those used in wildlife conservation problems for example, duck, geese, and swan eggs; and may be used with other endangered species such as reptiles, turtle eggs as well.

Similarly the invention may also be practiced with seed germination in wheat or corn. This latter application would probably require near infrared ranges of 0.1 to 3 microns whereas egg and embryo poultry would need the 3-12 micron range. Other crops such as bananas may also be used.

What is claimed is:

1. A method of detecting whether an egg is fertilized comprising the steps of providing a thermograph machine having a scanner, disposing an egg in proximity to the thermograph machine, scanning the egg with the scanner, providing a visual indication of any heat pattern from the egg as scanned by the thermograph machine, and comparing the visual indication with a reference heat pattern to determine if the visual indication is characteristic for a fertilized egg.

2. The method of claim 1 wherein the egg is a poultry egg.

3. The method of claim 1 wherein the visual indication is provided on a display screen.

4. The method of claim 1 wherein the visual indication is a thermograph.

5. The method of claim 1 wherein a series of eggs are mounted in at least one row on a conveyer belt passing through the view of the scanner.

6. The method of claim 5 wherein the eggs are poultry eggs in an incubation system, the visual indication being provided on a display screen, and including the step of removing unfertilized eggs from the incubation system.

7. The method of claim 6 wherein the eggs are arranged in multiple rows.

8. A method of detecting if eggs are diseased comprising the steps of providing a thermograph machine having a scanner, disposing an egg in proximity to the thermograph machine, scanning the egg with the scanner, providing a visual indication of any heat pattern from the egg as scanned by the thermograph machine, and comparing the visual indication with a reference heat pattern to determine if the visual indication is characteristic of a diseased egg.

* * * * *